(12) United States Patent
Casara et al.

(10) Patent No.: US 7,906,547 B2
(45) Date of Patent: Mar. 15, 2011

(54) AZABICYLIC COMPOUNDS, A PROCESS FOR THEIR PREPARATION AND PHARMACEUTICAL COMPOSITIONS CONTAINING THEM

(75) Inventors: Patrick Casara, Villennes sur Seine (FR); Anne-Marie Chollet, Le Pecq (FR); Alain Dhainaut, Chatou (FR); Pierre Lestage, La Celle St Cloud (FR); Fany Panayi, Paris (FR); Anita Roger, L'Etang-la-Ville (FR)

(73) Assignee: Les Laboratoires Servier, Suresnes Cedex (FR)

( * ) Notice: Subject to any disclaimer, the term of this patent is extended or adjusted under 35 U.S.C. 154(b) by 137 days.

(21) Appl. No.: 12/456,165

(22) Filed: Jun. 12, 2009

(65) Prior Publication Data
US 2009/0312389 A1   Dec. 17, 2009

Related U.S. Application Data

(60) Provisional application No. 61/132,257, filed on Jun. 17, 2008.

(30) Foreign Application Priority Data

Jun. 13, 2008   (FR) ...................... 08 03297

(51) Int. Cl.
*A61K 31/403* (2006.01)
*C07D 209/52* (2006.01)
(52) U.S. Cl. ...................... 514/412; 548/515
(58) Field of Classification Search .............. 548/515; 514/412
See application file for complete search history.

(56) References Cited

U.S. PATENT DOCUMENTS
2002/0035103 A1   3/2002   Bennani

FOREIGN PATENT DOCUMENTS

| EP | 1707203 | 10/2006 |
|---|---|---|
| WO | 2004/052857 | 6/2004 |
| WO | 2005/089747 | 9/2005 |
| WO | 2006/106425 | 10/2006 |
| WO | WO 2007/115798 | * 10/2007 |
| WO | 2008/010238 | 1/2008 |

OTHER PUBLICATIONS

Celanire et al. Drug Discover Today 2005, 10(23/24), 1613-1627.*
Esbenshade et al. Molecular Interventions 2006, 6(2), 77-88.*
Preliminary Search Report for FR0803297 of Jan. 30, 2009.

* cited by examiner

*Primary Examiner* — Jason M Nolan
(74) *Attorney, Agent, or Firm* — Hueschen and Sage

(57) ABSTRACT

Compounds of formula (I):

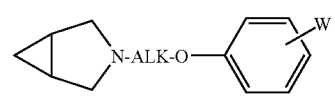

wherein:
ALK represents an alkylene chain,
W represents a group selected from

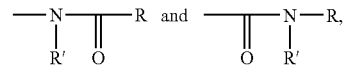

wherein R and R' are as defined in the description.
Medicinal products containing the same which are useful in the treatment of cognitive and psycho-behavioural disorders associated with cerebral ageing, with neurodegenerative diseases or with cranial traumas and also in the treatment of mood disorders, of schizophrenia and of cognitive disorders associated therewith, of sleep disorders, of sleep-waking rhythm disorders, of attention-deficit hyperactivity syndrome or of obesity.

20 Claims, No Drawings

AZABICYLIC COMPOUNDS, A PROCESS FOR THEIR PREPARATION AND PHARMACEUTICAL COMPOSITIONS CONTAINING THEM

The present invention relates to new azabicyclic compounds, to a process for their preparation and to pharmaceutical compositions containing them.

The compounds of the present invention are especially valuable from a pharmacological point of view for their interaction with central histaminergic systems in vivo.

Ageing of the population due to increased life expectancy at birth has brought with it a large increase in the incidence of age-related neuropathologies and especially of Alzheimer's disease. The principal clinical manifestations of cerebral ageing and especially of age-related neuropathologies are deficiencies in memory and cognitive functions, which may lead to dementia.

Neuropharmacological studies have shown that, in the central nervous system, histamine, via the central histaminergic systems, has the role of a neurotransmitter or neuromodulator in physiological or physiopathological situations (Pell and Green, *Annu. Rev. Neurosci.*, 1986, 9, 209-254; Schwartz et al., *Physiol Rev.*, 1991, 71, 1-51). Thus, it has been shown that histamine is involved in various physiological and behavioural processes, such as thermoregulation, neuro-endocrinal regulation, circadian rhythm, cataleptic states, motility, aggressiveness, eating behaviour, learning and memorisation, and synaptic plasticity (Hass et al., *Histaminergic neurones: morphology and function*, Boca Raton, Fla.: CRC Press, 1991, pp. 196-208; Brown et al., *Prog. Neurobiology*, 2001, 63, 637-672).

Studies carried out in animals have shown that an increase in endogenous extra-synaptic levels of histamine makes it possible to promote states of vigilance, learning and memory processes, and to regulate food intake (Brown et al., *Prog. Neurobiol.*, 2000, 63, 637-672; Passani et al., *Neurosci. Biobehav. Rev.*, 2000, 24, 107-113). As a result, the potential therapeutic indications for compounds capable of increasing the turnover or release of histamine at the central level are the treatment of cognitive deficiencies associated with cerebral ageing, with acute and chronic neurodegenerative diseases and with schizophrenia and also the treatment of mood disorders, of schizophrenia, of sleep disorders, of sleep-waking rhythm disorders and of attention-deficit hyperactivity syndrome. Furthermore, studies have shown that an injection of histamine into the central hypothalamic nuclei involved in the regulation of satiety attenuates feeding in the rat. Hypofunctioning of histaminergic transmission has moreover been demonstrated in genetically obese rats (Machidori et al., *Brain Research*, 1992, 590, 180-186). Consequently, eating behaviour disorders and obesity are also potential therapeutic indications for the compounds of the present invention.

The present invention relates to new azabicyclic compounds which are distinguished from the compounds mentioned in the Application WO2005/089747 by the presence of a 3-azabicyclo[3,1,0]hexane ring system.

Surprisingly, this structural difference from the compounds of the Application WO2005/089747 provides the compounds of the invention not only with remarkable pro-cognitive properties but also with powerful awakening, anti-sedative, anti-hypnotic and anti-depressant properties.

At the neurological level, this combination of activities opens the way not only to new treatments for cognitive disorders associated with cerebral ageing, with neurodegenerative diseases or with cranial traumas but also to the treatment of psycho-behavioural disorders associated with those pathologies, such as sleep disorders, apathy and/or depressive states. The pharmacological profile of the compounds of the invention moreover also makes it possible to envisage new treatments in the psychiatric field, for example for schizophrenia, mood disorders or sleep disorders.

The present invention relates, more specifically, to compounds of formula (I):

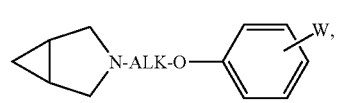

wherein:
ALK represents an alkylene chain,
W represents a group selected from

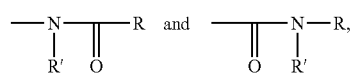

wherein R and R' represent, each independently of the other, a hydrogen or a linear or branched ($C_1$-$C_6$)alkyl group optionally substituted by one or more groups selected from halogen, hydroxy and alkoxy,
it being understood that:
the term "alkylene" denotes a linear or branched divalent radical containing from 2 to 6 carbon atoms,
the term "alkoxy" denotes an alkyl-oxy group in which the alkyl chain, which is linear or branched, contains from 1 to 6 carbon atoms,
to their enantiomers and diastereoisomers, and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Compounds of formula (I) to which preference is given are those wherein the W group is located in the para position.

ALK preferably represents an ethylene, propylene or butylene group, more preferably still a propylene group.

A particular embodiment of the invention relates to compounds of formula (I) wherein W represents a group —CO—$NH_2$, —NH—CO—$CH_3$, —N($CH_3$)—CO—$CH_3$ or —NH—CO—$CH_2$—$OCH_3$.

Even more especially, the invention relates to the compounds of formula (I) which are:
N-(4-{3-[(1R,5S)-3-azabicyclo[3.1.0]hex-3-yl]propoxy}phenyl)-N-methyl-acetamide,
N-(4-{2-[(1R,5S)-3-azabicyclo[3.1.0]hex-3-yl]ethoxy}phenyl)acetamide,
N-(4-{2-[(1R,5S)-3-azabicyclo[3.1.0]hex-3-yl]ethoxy}phenyl)-2-methoxy-acetamide,
4-{3-[(1R,5S)-3-azabicyclo[3.1.0]hex-3-yl]propoxy}benzamide, 4-{2-[(1R,5S)-3-azabicyclo[3.1.0]hex-3-yl]ethoxy}benzamide,
N-(4-{3-[(1R,5S)-3-azabicyclo[3.1.0]hex-3-yl]propoxy}phenyl)-2-methoxy-acetamide,
N-(4-{3-[(1R,5S)-3-azabicyclo[3.1.0]hex-3-yl]propoxy}phenyl)acetamide,
and addition salts thereof with a pharmaceutically acceptable acid or base.

Among the addition salts with a pharmaceutically acceptable acid, preference is given more especially to hydrochlorides, oxalates and citrates.

Preference is given to N-(4-{3-[(1R,5S)-3-azabicyclo[3.1.0]hex-3-yl]propoxy}phenyl)-N-methylacetamide hydrochloride.

4-{3-[(1R,5S)-3-Azabicyclo[3.1.0]hex-3-yl]propoxy}benzamide hydrochloride, 4-{3-[(1R,5S)-3-azabicyclo[3.1.0]hex-3-yl]propoxy}benzamide oxalate and 4-{3-[(1R,5S)-3-azabicyclo[3.1.0]hex-3-yl]propoxy}benzamide citrate are even more especially preferred.

The invention relates also to a process for the preparation of compounds of formula (I), which process is characterised in that there is used as starting material a compound of formula (II):

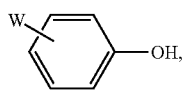

wherein W is as defined for formula (I),
with which compound of formula (II) there is condensed, in a basic medium, a compound of formula (III):

(III), wherein ALK is as defined for formula (I),
to obtain a compound of formula (IV):

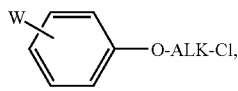

wherein W and ALK are as defined hereinbefore,
with which there is condensed the compound of formula (V):

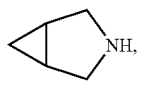

to yield a compound of formula (I) as defined hereinbefore:

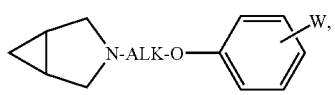

which may be purified according to a conventional separation technique, is converted, if desired, into its addition salts with a pharmaceutically acceptable acid or base and is separated, where appropriate, into its isomers according to a conventional separation technique.

The compounds of formulae (II), (III) and (V) are either commercially available or can be obtained by the person skilled in the art using conventional chemical reactions described in the literature.

Alternatively, compounds of formula (VI):

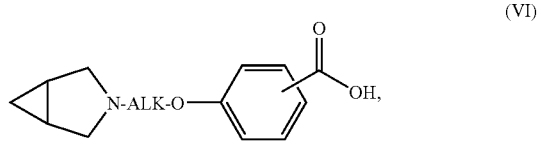

wherein the ALK group is as defined hereinbefore,
can be used as synthesis intermediates for compounds of formula (I) wherein W=—CONRR' by coupling with an amine of formula NHRR', wherein R and R' are as defined for formula (I).

The compounds of formula (I) wherein W=—CONRR' will be referred to as compounds of formula (I/a) hereinbelow.

Similarly, compounds of formula (VII):

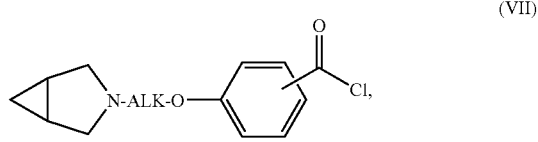

wherein the ALK group is as defined hereinbefore,
can be used as synthesis intermediates for compounds of formula (I/a) by coupling with an amine of formula NHRR', wherein R and R' are as defined for formula (I).

Furthermore, compounds of formula (I/a) can also be obtained by using compounds of formula (VIII) via the corresponding carboxylic acid (VI) and acyl chloride (VII) shown above:

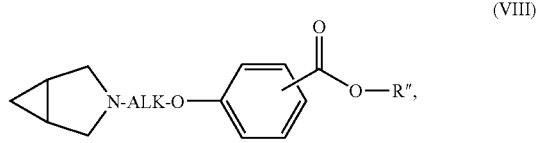

wherein the ALK group is as defined hereinbefore and R" represents a linear or branched ($C_1$-$C_6$)alkyl group.

Another alternative consists of using compounds of formula (VIII) in the presence of an amine of formula NHRR' to yield the compounds of formula (I/a) directly.

Finally, it is also possible to obtain compounds of formula (I/a) by hydrolysing compounds of formula (IX) in a basic medium:

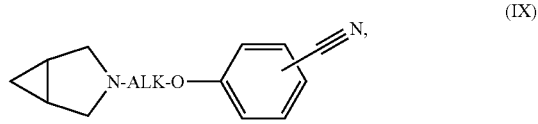

wherein the ALK group is as defined hereinbefore.

Pharmacological study of the compounds of formula (I) has shown that they have pro-cognitive properties by means of facilitating processes of memory and learning, and also awakening, anti-sedative, anti-hypnotic and anti-depressant properties. Furthermore, the compounds of formula (IX) also have pro-cognitive properties.

At the neurological level, the compounds according to the invention may be useful in the treatment of cognitive disorders associated with cerebral ageing or with neurodegenerative diseases such as Alzheimer's disease, Parkinson's disease, Pick's disease, Lewy body dementias, frontal and subcortical dementias, frontotemporal dementias, vascular dementias, Huntington's disease and multiple sclerosis, in new treatments for cognitive disorders associated with cranial traumas, but also in the treatment of psycho-behavioural disorders associated with those pathologies such as sleep disorders, apathy and depression. Sleep disorders associated with Alzheimer's disease and with Parkinson's disease, such as diurnal hypersomnolence, especially are targets.

At the psychiatric level, these compounds can be useful in the treatment of mood disorders, and more especially in the treatment of depressive states, of schizophrenia and of cognitive disorders associated therewith, and also in the treatment of sleep disorders, of sleep-waking rhythm disorders and of attention-deficit hyperactivity syndrome (ADHD). Among the sleep disorders there may be more especially mentioned narcolepsy, hypersomnia occurring in obstructive sleep apnea syndrome or in attention-deficit hyperactivity syndrome, and also diurnal somnolence.

The present invention relates also to pharmaceutical compositions comprising at least one compound of formula (I) on its own or in combination with one or more pharmaceutically acceptable excipients.

In the pharmaceutical compositions according to the invention, the weight proportion of active ingredient (weight of the active ingredient over the total weight of the composition) is from 1 to 50%.

Among the pharmaceutical compositions according to the invention, there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The useful dosage varies according to the sex, age and weight of the patient, the administration route, the nature of the therapeutic indication, and any associated treatments, and ranges from 0.05 mg to 500 mg per 24 hours for treatment in from 1 to 3 administrations per day.

The following Examples illustrate the invention but do not limit it in any way The structures of the compounds described in the Examples were determined in accordance with the usual spectrophotometric techniques (infrared, NMR, mass spectrometry etc.).

By way of information, all the compounds hereinbelow have meso-type stereochemistry.

EXAMPLE 1

Synthesis Route A: 4-{3-[(1R,5S)-3-Azabicyclo[3.1.0]hex-3-yl]propoxy}-benzamide hydrochloride Step 1: 4-(3-Chloropropoxy)benzamide A mixture composed of 0.004 mole of 4-hydroxybenzamide, 0.004 mole of 1-bromo-3-chloropropane and 0.006 mole of caesium carbonate in 10 ml of acetonitrile is heated at reflux for 5 hours.

Step 2: 4-{3-[(1R,5S)-3-Azabicyclo[3.1.0]hex-3-yl]propoxy}benzamide 0.004 mole of (1R,5S)-3-azabicyclo[3.1.0]hexane and 0.002 mole of sodium iodide are added to the reaction mixture of Step 1 at ambient temperature. Refluxing is then resumed for 16 hours. The precipitate is filtered off and rinsed with acetonitrile. The filtrate is concentrated to dryness. The residue is taken up in dichloromethane. The resulting solution is extracted with sodium hydroxide solution and then with water, before being dried over magnesium sulphate and concentrated to dryness. The residue is purified by a preparative chromatography technique on a Lichroprep RP-18 phase.

Mass spectrum: $[M+H]^+$ theoretical m/z=243.1510; experimental m/z=243.1497

Step 3: 4-{3-[(1R,5S)-3-Azabicyclo[3.1.0]hex-3-yl]propoxy}benzamide hydrochloride The product obtained in Step 2 is dissolved in 10 ml of ethanol, to which there are added 2 ml of 2N ethereal HCl solution. The crystallised product is filtered off, rinsed with ethanol and dried in vacuo.

Elemental Microanalysis:

|  | % C | % H | % N | % Cl | % Cl⁻ |
|---|---|---|---|---|---|
| Calculated | 60.70 | 7.13 | 9.44 | 11.95 | 11.95 |
| Found | 60.74 | 7.04 | 9.31 | 11.89 | 11.87 |

EXAMPLE 1

Route B: 4-{3-[(1R,5S)-3-Azabicyclo[3.1.0]hex-3-yl]propoxy}benzamide hydrochloride Step 1: 4-{3-[(1R,5S)-3-Azabicyclo[3.1.0]hex-3-yl]propoxy}benzonitrile The experimental procedure is the same as Steps 1 and 2 of Example 1, synthesis route A, but replacing the 4-hydroxybenzamide in Step 1 by 4-hydroxybenzonitrile.

Mass spectrum: $[M+H]^+$ theoretical m/z=243.1510; experimental m/z=243.1497

Step 2: 4-{3-[(1R,5S)-3-Azabicyclo[3.1.0]hex-3-yl]propoxy}benzamide hydrochloride The compound obtained in the Step above (2.2 g) is dissolved in 90 ml of ethanol and refluxed in the presence of 5.1 g of KOH for 18 hours. The mixture is poured into 90 ml of water and is then concentrated to half volume in vacuo. The solid obtained is filtered off, rinsed with isopropyl ether and then dried. The hydrochloride is prepared according to the operating procedure of Step 3 of Example 1, synthesis route A.

Elemental Microanalysis:

|  | % C | % H | % N | % Cl | % Cl⁻ |
|---|---|---|---|---|---|
| Calculated | 60.70 | 7.13 | 9.44 | 11.95 | 11.95 |
| Found | 60.36 | 7.11 | 9.11 | 11.36 | 11.93 |

EXAMPLE 1

Route C: 4-{3-[(1R,5S)-3-Azabicyclo[3.1.0]hex-3-yl]propoxy}benzamide hydrochloride

Step 1: Methyl 4-{3-[(1R,5S)-3-azabicyclo[3.1.0]hex-3-yl]propoxy}benzoate

The experimental procedure is the same as Steps 1 and 2 of Example 1, synthesis route A, but replacing the 4-hydroxybenzamide in Step 1 by methyl 4-hydroxybenzoate.

Step 2: 4-{3-[(1R,5S)-3-Azabicyclo[3.1.0]hex-3-yl]propoxy}benzoic acid

A mixture of 3.5 g of the compound of Step 1, 12.7 ml of 2N sodium hydroxide solution and 8 ml of methanol is refluxed for one hour. To the reaction mixture, cooled in an ice bath, there are added 12.7 ml of 2N HCl. The precipitate is washed with water and dried in vacuo.

Elemental Microanalysis:

|  | % C | % H | % N |
|---|---|---|---|
| Calculated | 68.94 | 7.33 | 5.36 |
| Found | 68.74 | 7.32 | 5.42 |

Step 3: 4-{3-[(1R,5S)-3-Azabicyclo[3.1.0]hex-3-yl]propoxy}benzoyl chloride hydrochloride A mixture of 1.8 g of the product described in Step 2 and 20 ml of thionyl chloride is refluxed for 2 hours. The reaction mixture is concentrated in vacuo and co-evaporated twice with toluene. The solid residue is homogenised in ethyl ether, filtered off and dried in vacuo.

Step 4: 4-{3-[(1R,5S)-3-Azabicyclo[3.1.0]hex-3-yl]propoxy}benzamide hydrochloride 2 ml of 2N ammoniacal methanol are added dropwise to a solution of 1 g of the product described in Step 3 in dichloromethane at 0° C. The mixture is then stirred for 1 hour at ambient temperature and is washed with 2N sodium hydroxide solution and then with water. The organic phase is dried over magnesium sulphate and concentrated. The residual oil is dissolved in 10 ml of ethanol to which 2 ml of 2N ethereal HCl solution are added. The crystallised product is filtered off, rinsed with ethanol and dried in vacuo.

Elemental Microanalysis:

|  | % C | % H | % N | % Cl |
|---|---|---|---|---|
| Calculated | 60.70 | 7.13 | 9.44 | 11.95 |
| Found | 60.74 | 7.04 | 9.31 | 11.89 |

EXAMPLE 2

4-{2-[(1R,5S)-3-Azabicyclo[3.1.0]hex-3-yl]ethoxy}benzamide

The experimental procedure is the same as Steps 1 and 2 of Example 1, synthesis route A, but replacing the 1-bromo-3-chloropropane in Step 1 by 1-bromo-2-chloroethane.

Elemental Microanalysis:

|  | % C | % H | % N |
|---|---|---|---|
| Calculated | 68.27 | 7.37 | 11.37 |
| Found | 67.07 | 7.12 | 11.15 |

EXAMPLE 3

4-{4-[(1R,5S)-3-Azabicyclo[3.1.0]hex-3-yl]butoxy}benzamide

The experimental procedure is the same as Steps 1 and 2 of Example 1, synthesis route A, but replacing the 1-bromo-3-chloropropane in Step 1 by 1-bromo-4-chlorobutane.

Elemental Microanalysis:

|  | % C | % H | % N |
|---|---|---|---|
| Calculated | 70.04 | 8.08 | 10.21 |
| Found | 69.96 | 8.07 | 9.91 |

EXAMPLE 4

N-(4-{3-[(1R,5S)-3-Azabicyclo[3.1.0]hex-3-yl]propoxy}phenyl)acetamide

The experimental procedure is the same as Steps 1 and 2 of Example 1, but replacing the 4-hydroxybenzamide in Step 1 by N-(4-hydroxyphenyl)acetamide.

Elemental Microanalysis:

|  | % C | % H | % N |
|---|---|---|---|
| Calculated | 70.04 | 8.08 | 10.21 |
| Found | 69.77 | 8.02 | 10.00 |

EXAMPLE 5

N-(4-{2-[(1R,5S)-3-Azabicyclo[3.1.0]hex-3-yl]ethoxy}phenyl)acetamide

The experimental procedure is the same as Steps 1 and 2 of Example 2, but replacing the 4-hydroxybenzamide in Step 1 by N-(4-hydroxyphenyl)acetamide.

Elemental Microanalysis:

|  | % C | % H | % N |
|---|---|---|---|
| Calculated | 69.21 | 7.74 | 10.76 |
| Found | 68.86 | 7.66 | 10.55 |

EXAMPLE 6

N-(4-{4-[(1R,5S)-3-Azabicyclo[3.1.0]hex-3-yl]butoxy}phenyl)acetamide

The experimental procedure is the same as Steps 1 and 2 of Example 3, but replacing the 4-hydroxybenzamide in Step 1 by N-(4-hydroxyphenyl)acetamide.

Elemental Microanalysis:

|  | % C | % H | % N |
|---|---|---|---|
| Calculated | 70.80 | 8.39 | 9.71 |
| Found | 70.44 | 8.35 | 9.14 |

EXAMPLE 7

4-{3-[(1R,5S)-3-Azabicyclo[3.1.0]hex-3-yl]propoxy}-N,N-dimethyl-benzamide

The experimental procedure is the same as Steps 1 and 2 of Example 1, synthesis route A, but replacing the 4-hydroxybenzamide in Step 1 by 4-hydroxy-N,N-dimethylbenzamide.

Elemental Microanalysis:

|  | % C | % H | % N |
|---|---|---|---|
| Calculated | 70.80 | 8.39 | 9.71 |
| Found | 70.82 | 8.32 | 9.60 |

EXAMPLE 8

4-{4-[(1R,5S)-3-Azabicyclo[3.1.0]hex-3-yl]butoxy}-N,N-dimethyl-benzamide oxalate The experimental procedure is the same as Steps 1 and 2 of Example 3, but replacing the 4-hydroxybenzamide in Step 1 by 4-hydroxy-N,N-dimethylbenzamide. Then, to 0.38 g of the compound thereby obtained in 6 ml of ethanol, there is added 0.32 g of oxalic acid. The product obtained is filtered off, rinsed with ethyl ether and then dried in vacuo.

Elemental Microanalysis:

|  | % C | % H | % N |
|---|---|---|---|
| Calculated | 61.21 | 7.19 | 7.14 |
| Found | 60.13 | 6.93 | 6.71 |

EXAMPLE 9

4-{3-[(1R,5S)-3-Azabicyclo[3.1.0]hex-3-yl]propoxy}-N,N-diethylbenzamide hydrochloride The experimental procedure is the same as that of Example 1, synthesis route A, but replacing the 4-hydroxybenzamide in Step 1 by 4-hydroxy-N,N-diethylbenzamide.

Elemental Microanalysis:

|  | % C | % H | % N | % Cl | % Cl⁻ |
|---|---|---|---|---|---|
| Calculated | 64.67 | 8.28 | 7.94 | 10.05 | 10.05 |
| Found | 64.92 | 7.59 | 8.24 | 12.57 | 10.78 |

EXAMPLE 10

4-{4-[(1R,5S)-3-Azabicyclo[3.1.0]hex-3-yl]butoxy}-N,N-diethyl-benzamide

The experimental procedure is the same as Steps 1 and 2 of Example 3, but replacing the 4-hydroxybenzamide in Step 1 by 4-hydroxy-N,N-diethylbenzamide.

Elemental Microanalysis:

|  | % C | % H | % N |
|---|---|---|---|
| Calculated | 72.69 | 9.15 | 8.48 |
| Found | 72.45 | 9.02 | 8.33 |

EXAMPLE 11

4-{3-[(1R,5S)-3-Azabicyclo[3.1.0]hex-3-yl]propoxy}-N-methylbenzamide

The experimental procedure is the same as Steps 1 and 2 of Example 1, synthesis route A, but replacing the 4-hydroxybenzamide in Step 1 by 4-hydroxy-N-methylbenzamide.

Elemental Microanalysis:

|  | % C | % H | % N |
|---|---|---|---|
| Calculated | 70.04 | 8.08 | 10.21 |
| Found | 69.93 | 8.00 | 10.09 |

EXAMPLE 12

4-{4-[(1R,5S)-3-Azabicyclo[3.1.0]hex-3-yl]butoxy}-N-methylbenzamide

The experimental procedure is the same as Steps 1 and 2 of Example 3, but replacing the 4-hydroxybenzamide in Step 1 by 4-hydroxy-N-methylbenzamide.

Elemental Microanalysis:

|  | % C | % H | % N |
| --- | --- | --- | --- |
| Calculated | 70.80 | 8.39 | 9.71 |
| Found | 69.66 | 8.17 | 9.20 |

EXAMPLE 13

N-(4-{3-[(1R,5S)-3-Azabicyclo[3.1.0]hex-3-yl]propoxy}phenyl)-N-methylacetamide hydrochloride The experimental procedure is the same as that of Example 1, synthesis route A, but replacing the 4-hydroxybenzamide in Step 1 by N-(4-hydroxyphenyl)-N-methylacetamide.

Elemental Microanalysis:

|  | % C | % H | % N | % Cl | % Cl⁻ |
| --- | --- | --- | --- | --- | --- |
| Calculated | 62.86 | 7.76 | 8.62 | 10.91 | 10.91 |
| Found | 62.27 | 7.56 | 8.46 | 11.62 | 11.29 |

EXAMPLE 14

N-(4-{3-[(1R,5S)-3-Azabicyclo[3.1.0]hex-3-yl]propoxy}phenyl)-2-methoxyacetamide The experimental procedure is the same as Steps 1 and 2 of Example 1, synthesis route A, but replacing the 4-hydroxybenzamide in Step 1 by N-(4-hydroxyphenyl)-2-methoxyacetamide.

Elemental Microanalysis:

|  | % C | % H | % N |
| --- | --- | --- | --- |
| Calculated | 67.08 | 7.95 | 9.20 |
| Found | 66.72 | 7.92 | 9.18 |

EXAMPLE 15

N-(4-{2-[(1R,5S)-3-Azabicyclo[3.1.0]hex-3-yl]ethoxy}phenyl)-2-methoxyacetamide The experimental procedure is the same as Steps 1 and 2 of Example 2, but replacing the 4-hydroxybenzamide in Step 1 by N-(4-hydroxyphenyl)-2-methoxyacetamide.

Elemental Microanalysis:

|  | % C | % H | % N |
| --- | --- | --- | --- |
| Calculated | 66.19 | 7.64 | 9.65 |
| Found | 65.9 | 7.50 | 9.44 |

EXAMPLE 16

N-(4-{4-[(1R,5S)-3-Azabicyclo[3.1.0]hex-3-yl]butoxy}phenyl)-N-methylacetamide hydrochloride The experimental procedure is the same as that of Example 13, but replacing the 1-bromo-3-chloropropane in Step 1 by 1-bromo-4-chlorobutane.

Elemental Microanalysis:

|  | % C | % H | % N | % Cl | % Cl⁻ |
| --- | --- | --- | --- | --- | --- |
| Calculated | 65.47 | 8.52 | 7.63 | 9.66 | 9.66 |
| Found | 65.35 | 8.41 | 7.30 | 9.80 | 9.67 |

EXAMPLE 17

N-(4-{4-[(1R,5S)-3-Azabicyclo[3.1.0]hex-3-yl]butoxy}phenyl)-2-methoxyacetamide hydrochloride The experimental procedure is the same as that of Example 1, synthesis route A but, in Step 1, replacing the 4-hydroxybenzamide by N-(4-hydroxyphenyl)-2-methoxyacetamide and the 1-bromo-3-chloropropane by 1-bromo-4-chlorobutane.

Elemental Microanalysis:

|  | % C | % H | % N | % Cl | % Cl⁻ |
| --- | --- | --- | --- | --- | --- |
| Calculated | 62.73 | 8.16 | 7.32 | 9.27 | 9.26 |
| Found | 61.92 | 7.89 | 6.99 | 9.90 | 9.62 |

EXAMPLE 18

4-{3-[(1R,5S)-3-Azabicyclo[3.1.0]hex-3-yl]propoxy}benzamide

The experimental procedure repeats Steps 1 and 2 of Example 1, synthesis route A.

Elemental Microanalysis:

|  | % C | % H | % N |
| --- | --- | --- | --- |
| Calculated | 69.21 | 7.74 | 10.76 |
| Found | 69.24 | 7.69 | 10.60 |

EXAMPLE 19

4-{3-[(1R,5S)-3-Azabicyclo[3.1.0]hex-3-yl]propoxy}benzamide oxalate

The experimental procedure repeats Steps 1 and 2 of Example 1, synthesis route A. The compound thereby obtained is converted into a salt according to the operating procedure described in Example 8.

Elemental Microanalysis:

|  | % C | % H | % N |
|---|---|---|---|
| Calculated | 56.73 | 6.13 | 7.60 |
| Found | 55.98 | 6.28 | 6.94 |

EXAMPLE 20

4-{3-[(1R,5S)-3-Azabicyclo[3.1.0]hex-3-yl]propoxy}benzamide citrate

One equivalent of the compound of Example 18, in the presence of 1.2 equivalents of citric acid monohydrate, is dissolved in water to yield the title product.

$^1$H NMR (600 MHz; DMSO-d$_6$): δ (ppm)=9.5-12.5 (sl, 3H); 7.85 (m, 3H); 7.20 (sl, 1H); 6.95 (m, 2H); 4.05 (t, 2H); 3.30 (dl, 2H); 2.80-3 (2 sl, 4H); 2.65 (d, 2H); 2.55 (d, 2H); 1.95 (qt, 2H); 1.6 (sl, 2H); 0.5-0.7 (2 m, 2H).

Pharmacological Study

EXAMPLE A

Cerebral Levels of N$^τ$-methylhistamine in the NMRI Mouse

The purpose of this study, which was carried out in accordance with the method of Taylor et al. (Biochem. Pharm., 1992, 44, 1261-1267), is to evaluate the ex vivo activity of the compounds of the present invention as antagonists of type H$_3$ central histamine receptors. That activity is revealed by measuring, after treatment with the test compounds by the oral route, the central levels of N$^τ$-methylhistamine, which is a main metabolite of histamine. An increase in the cerebral concentrations of N$^τ$-methylhistamine indicates an increase in the turn-over of histamine by blockage of the type H$_3$ central histamine receptors.

NMRI mice (18-20 g) are treated with compounds of the present invention or with their carrier (20 ml/kg) by the oral route. One hour after the pharmacological treatment, the animals are sacrificed; the brains are removed, frozen in liquid nitrogen, weighed and homogenised in 0.1N HClO$_4$ at 4° C. The homogenised products are centrifuged (15 000 g, 17 min, 4° C.). The supernatants are recovered and divided into aliquots. The aliquots are frozen in liquid nitrogen and stored at −80° C. until they are analysed.

Determination of the cerebral levels of N$^τ$-methylhistamine is carried out by capillary electrophoresis. The tissue levels of N$^τ$-methylhistamine are expressed in μg/g of fresh brain. The comparison of the cerebral levels of N$^τ$-methylhistamine between animals treated with the carrier (controls) and animals treated with compounds of the present invention is carried out by single-factor variance analysis followed, if necessary, by a complementary analysis (Dunnett's test).

The results show that, at doses of from 1 to 30 mg/kg PO, the compounds of the present invention are capable of increasing endogenous cerebral concentrations of N$^τ$-methyl-histamine by more than 200% in concentration-dependent manner.

By way of example, compounds 1, 5, 6, 13 and 14 increase the endogenous cerebral concentrations of N$^τ$-methylhistamine by 99%, 109%, 106%, 135% and 124%, respectively, when administered at 10 mg/kg PO, and by 227%, 200%, 210%, 303% and 266%, respectively, at the 30 mg/kg PO dose. These results demonstrate that the compounds of the present invention are powerful antagonists of type H$_3$ central histamine receptors.

EXAMPLE B

Electroencephalogram Recordings in the Awake Wistar Rat

Electrodes are chronically implanted in adult male Wistar rats, being located at the surface of the frontal and parietal cortex. Cortical electroencephalogram (EEG) recordings are made in the rats placed in cages in a sound-proofed room. The compounds and carriers are administered in randomised manner by the intraperitoneal route at 10 o'clock on the same days with a minimum of 3 days between each administration, allowing each rat to be used as its own control. The absolute power of the slow delta activities (1-4 Hz), which predominate during slow sleep and disappear during wakefulness and paradoxical sleep, is averaged over successive periods of 30 minutes. Over 30 minutes, high and low values for the power of the slow delta activities are signs of wakefulness and of sleep, respectively. The results show that the compounds of the present invention increase cortical wakefulness (reduction in delta waves) in the rat.

By way of example, compounds 1 and 13 administered at the 3 mg/kg IP dose, cause a significant reduction in the power of the slow delta waves for 120 minutes, a sign of cortical activation and wakefulness.

EXAMPLE C

Interaction with Barbital in the Wistar Rat

The objective of this test is to determine the anti-sedative, awakening and/or anti-hypnotic properties of the compounds of the present invention. The rats are placed in individual cages and are given an injection of barbital (170 mg/kg IP). The duration of sleep is then measured for 4 hours after the injection of barbital, determined on the basis of loss of the righting reflex. The compounds of the invention or their carriers are administered by the oral route 30 minutes before the administration of barbital. The results demonstrate that the compounds of the present invention have powerful anti-sedative, anti-hypnotic and/or awakening activities.

For example, at the 30 mg/kg PO dose, compounds 5, 8, 12 and 15 reduce the duration of sleeping caused by the barbital by −80%, −79%, −55% and −76%, respectively.

EXAMPLE D

Object Recognition in the Sprague-Dawley Rat

The object recognition test in the Sprague-Dawley rat (Behav. Brain Res., 1988, 31, 47-59) is based on the spontaneous exploratory activity of the animal and has the characteristics of episodic memory in humans. This memory test is sensitive to ageing (Eur. J. Pharmacol., 1997, 325, 173-180) and to cholinergic dysfunctions (Pharm. Biochem. Behav. 1996, 53(2), 277-283) and is based on the differences in the exploration of 2 objects of fairly similar shape—one familiar, the other new. Prior to the test, the animals are habituated to the environment (an enclosure without an object). In the course of a first session, the rats are placed (3 minutes) in the enclosure, in which there are 2 identical objects. The duration of exploration is measured for each object. In the course of the second session (3 minutes), 24 hours later, 1 of the 2 objects is replaced by a new object. The duration of exploration is measured for each object. The assessment criterion is the difference, Delta, expressed in seconds, between the exploration times for the new object and for the familiar object in the course of the second session. The control animals, previously treated with the carrier by the oral route 60 minutes before each session, explore the familiar object and the new object in an identical manner, which indicates that the object introduced earlier has been forgotten. Animals treated with a compound that facilitates mnemocognition preferentially explore the new object, which indicates that the object introduced earlier has been remembered. For Example, the results obtained with Example 1 of the present invention show a difference, Delta, of the order of 6 s, at the 0.3 mg/kg PO dose, which shows that the compounds of the invention greatly enhance memorisation, even at a very low dose.

EXAMPLE E

Social Recognition in the Wistar Rat

Initially described in 1982 (J. Comp. Physiol., 1982, 96, 1000-1006), the social recognition test has subsequently been proposed by various authors (Psychopharmacology, 1987, 91, 363-368; Psychopharmacology, 1989, 97, 262-268) for studying the mnemocognitive effects of new compounds. The test is based on the natural expression of the olfactory memory of the rat and its natural tendency to forget and allows evaluation of memorisation, by recognition of a young congeneric animal, by an adult rat. A young rat (21 days), taken at random, is placed for 5 minutes in the cage housing an adult rat. With the aid of a video device, the experimenter observes the social recognition behaviour of the adult rat and measures its overall duration. The young rat is then removed from the adult rat's cage and is placed in its own cage until the second introduction. The adult rat is given the compound under test by the intraperitoneal route and, after 2 hours, is again brought into the presence (5 minutes) of the young rat. The social recognition behaviour is then observed again and its duration measured. The assessment criterion is the difference (T2–T1), expressed in seconds, between the "recognition" times of the 2 encounters. The results obtained with Example 1 show a difference (T2–T1) of 21 s and 26 s for doses of 1 and 3 mg/kg IP, respectively, which shows that the compounds of the invention very greatly enhance memorisation, even at a low dose.

EXAMPLE F

Marble-Burying Test in the NMRI Mouse

The spontaneous marble-burying behaviour in the mouse is a very sensitive empirical test for antidepressant compounds (Sanchez and Meier, Psychopharmacology, 1997; 129: 197-205; Nicolas and Prinssen, Eur. J. Pharmacol., 2006, 547: 106-115). The mice are placed in individual cages in which there are 24 marbles and the number of marbles buried by each animal is determined for a period of 30 minutes. The animals are treated by the intraperitoneal route with the compounds of the present invention or their carriers 30 minutes before placing the animals in the cage containing marbles.

The results demonstrate, for example, that, at the 30 mg/kg IP dose, compounds 1, 2, 5 and 15 bring about a decrease in the number of balls buried of 48%, 99%, 49% and 83%, respectively.

This result demonstrates that the compounds of the present invention have antidepressant properties.

EXAMPLE G

Tail Suspension Test in the NMRI Mouse

The tail suspension test in the mouse (Porsolt et al., Arch. Int. Pharmacodyn., 1987, 288, 11) enables detection of psychopharmacological properties of compounds. NMRI mice are suspended by the tail, with the aid of a piece of adhesive tape, from a hook for 6 minutes: the immobility time is measured automatically with the aid of movement sensors. The animals are treated, by the intraperitoneal route, with the compounds of the invention or their carriers 24 hours and 30 minutes before they are suspended.

The results show that Examples 1, 4, 5, 13, 14 and 15, when administered at the 10 mg/kg IP dose, cause reductions in the immobility time of 59%, 36%, 64%, 53%, 36% and 77%, respectively. This result confirms the antidepressant properties of the compounds of the present invention.

EXAMPLE H

Forced Swimming Test in the NMRI Mouse

The forced swimming test is very widely used for detecting the antidepressant properties of compounds (Porsolt et al., Arch. Int. Pharmacodyn., 1977, 229, 327-336). The animals are placed for 6 minutes in cylinders filled with water (14 cm) and the immobility time is measured for the final 4 minutes by a video-tracking system. The compounds of the present invention or their carriers are administered by the intraperitoneal route 30 minutes before the mice are placed in the cylinder.

Examples 1, 5 and 15, at the 30 mg/kg IP dose, cause reductions in immobility of 76%, 32% and 34%, respectively. The results are indicative of the antidepressant properties of the compounds of the present invention.

EXAMPLE I

Pharmaceutical Compositions

Preparation formula for 1000 tablets each containing 100 mg of active ingredient:

| | |
|---|---|
| Compound of Example 1 | 100 g |
| Hydroxypropylcellulose | 20 g |
| Polyvinylpyrrolidone | 20 g |
| Wheat starch | 150 g |
| Lactose | 900 g |
| Magnesium stearate | 30 g |

The invention claimed is:

1. A compound selected from those of formula (I):

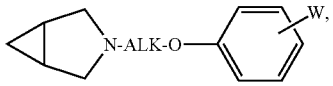

wherein:
ALK represents an alkylene chain,
W represents a group selected from

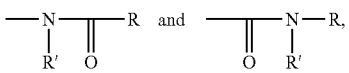

wherein R and R' represent, each independently of the other, a hydrogen or a linear or branched $(C_1-C_6)$alkyl group optionally substituted by one or more groups selected from halogen, hydroxy and alkoxy,
it being understood that:
the term "alkylene" denotes a linear or branched divalent radical having from 2 to 6 carbon atoms,
the term "alkoxy" denotes an alkyl-oxy group in which the alkyl chain, which is linear or branched, has from 1 to 6 carbon atoms,
its enantiomers, diastereoisomers, and addition salts thereof with a pharmaceutically acceptable acid or base.

2. The compound of claim 1, wherein the W group is located in the para position.

3. The compound of claim 1, wherein ALK represents an ethylene, propylene or butylene group.

4. The compound of claim 1, wherein ALK represents a propylene group.

5. The compound of claim 1, wherein W represents —CO—NH$_2$, —NH—CO—CH$_3$, —N(CH$_3$)—CO—CH$_3$ or —NH—CO—CH$_2$—OCH$_3$.

6. The compound of claim 1, wherein W represents —CO—NH$_2$.

7. The compound of claim 1, which is selected from:
N-(4-{3-[(1R,5S)-3-azabicyclo[3.1.0]hex-3-yl]propoxy}phenyl)-N-methyl-acetamide,
N-(4-{2-[(1R,5S)-3-azabicyclo[3.1.0]hex-3-yl]ethoxy}phenyl)acetamide,
N-(4-{2-[(1R,5S)-3-azabicyclo[3.1.0]hex-3-yl]ethoxy}phenyl)-2-methoxyacetamide,
4-{3-[(1R,5S)-3-azabicyclo[3.1.0]hex-3-yl]propoxy}benzamide,
4-{2-[(1R,5S)-3-azabicyclo[3.1.0]hex-3-yl]ethoxy}benzamide,
N-(4-{3-[(1R,5S)-3-azabicyclo[3.1.0]hex-3-yl]propoxy}phenyl)-2-methoxyacetamide,
N-(4-{3-[(1R,5S)-3-azabicyclo[3.1.0]hex-3-yl]propoxy}phenyl)acetamide,
and addition salts thereof with a pharmaceutically acceptable acid or base.

8. The compound of claim 1, which is 4-{3-[(1R,5S)-3-azabicyclo[3.1.0]hex-3-yl]-propoxy}benzamide hydrochloride.

9. The compound of claim 1, which is 4-{3-[(1R,5S)-3-azabicyclo[3.1.0]hex-3-yl]-propoxy}benzamide oxalate.

10. The compound of claim 1, which is 4-{3-[(1R,5S)-3-azabicyclo[3.1.0]hex-3-yl]-propoxy}benzamide citrate.

11. A compound selected from those of formula (VI):

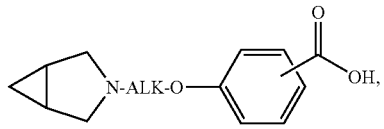

wherein ALK represents an alkylene chain.

12. A compound selected from those of (VII):

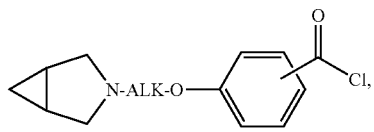

wherein ALK represents an alkylene chain.

13. A compound selected from those of formula (VIII):

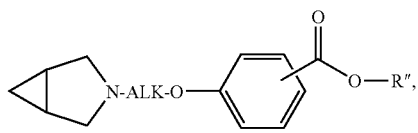

ALK represents an alkylene chain and R" represents a linear or branched $(C_1-C_6)$alkyl group.

14. A compound selected from those of formula (IX):

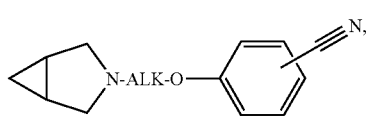

wherein ALK represents an alkylene chain.

15. A pharmaceutical composition comprising as active ingredient at least one compound of claim 1, alone or in combination with one or more pharmaceutically acceptable excipients.

16. A method of treating a living animal body, including a human, afflicted with a condition selected from cognitive and psycho-behavioural disorders associated with cerebral aging; cognitive and psycho-behavioural disorders associated with neurodegenerative diseases; cognitive and psycho-behavioural disorders associated with cranial traumas; mood disorders; schizophrenia; cognitive disorders associated with schizophrenia; sleep disorders; sleep-waking rhythm disorders; attention-deficit hyperactivity syndrome; and obesity, such method comprising the step of administering to the living animal body, including a human, a therapeutically effective amount of a compound of claim 1.

17. The method of claim 16, wherein the condition is selected from cognitive and psycho-behavioural disorders associated with Alzheimer's disease; cognitive and psycho-behavioural disorders associated with Parkinson's disease; cognitive and psycho-behavioural disorders associated with Pick's disease; cognitive and psycho-behavioural disorders associated with Lewy body dementias; cognitive and psycho-behavioural disorders associated with frontal and subcortical dementias; cognitive and psycho-behavioural disorders associated with frontotemporal dementias; cognitive and psycho-behavioural disorders associated with vascular dementias; cognitive and psycho-behavioural disorders associated with Huntington's disease; and cognitive and psycho-behavioural disorders associated with multiple sclerosis.

18. The method of claim 16, wherein the condition is a psycho-behavioural disorder selected from sleep disorders, apathy, and depressive states.

19. The method of claim 16, wherein the condition is selected from sleep disorders, including narcolepsy and hypersomnia occurring in obstructive sleep apnea syndrome; attention-deficit hyperactivity syndrome; and diurnal somnolence.

20. The method of claim 17, wherein the condition is selected from sleep disorders associated with Alzheimer's disease and sleep disorders associated with Parkinson's disease.

* * * * *